United States Patent [19]

Pilat et al.

[11] 4,345,093

[45] Aug. 17, 1982

[54] ETHYLENE RECOVERY FROM ETHYL ACRYLATE PROCESS

[75] Inventors: Howard L. Pilat, Dallas; Jerry D. Moore, Houston; Jack Chosnek, Corpus Christi, all of Tex.

[73] Assignee: Celanese Corporation, New York, N.Y.

[21] Appl. No.: 278,547

[22] Filed: Jun. 29, 1981

[51] Int. Cl.³ ............... C07C 69/54; C07C 139/08
[52] U.S. Cl. ................... 560/205; 260/460
[58] Field of Search ............ 560/205, 217, 234, 235; 260/460

[56] References Cited

U.S. PATENT DOCUMENTS

| | | | |
|---|---|---|---|
| 1,993,421 | 3/1935 | Stuart | 260/460 |
| 2,755,297 | 7/1956 | Smith et al. | 260/460 |
| 3,703,539 | 11/1972 | Di Liddo | 560/217 |
| 3,894,076 | 7/1975 | Van Duyne et al. | 560/217 |

*Primary Examiner*—Natalie Trousof
*Assistant Examiner*—L. Hendriksen
*Attorney, Agent, or Firm*—Stewart N. Rice

[57] ABSTRACT

Unreacted ethylene contained in a gaseous light ends stream derived from a process for the production of ethyl acrylate from ethylene and acrylic acid utilizing a sulfuric acid catalyst, is recovered by intimately contacting, under controlled conditions of temperature and pressure, the light ends stream with the liquid sulfuric acid catalyst make-up stream which is passed to the ethyl acrylate process. Upon contact of the light ends stream with the sulfuric acid make-up stream, the ethylene reacts with sulfuric acid to form ethyl hydrogen sulfate and diethyl sulfate, both of which remain in solution in the sulfuric acid which is then passed to the ethyl acrylate process as a source of make-up sulfuric acid. Sulfur dioxide contained in the vent-gas stream is not absorbed into the sulfuric acid, and therefore not recycled to the ethyl acrylate process.

4 Claims, 1 Drawing Figure

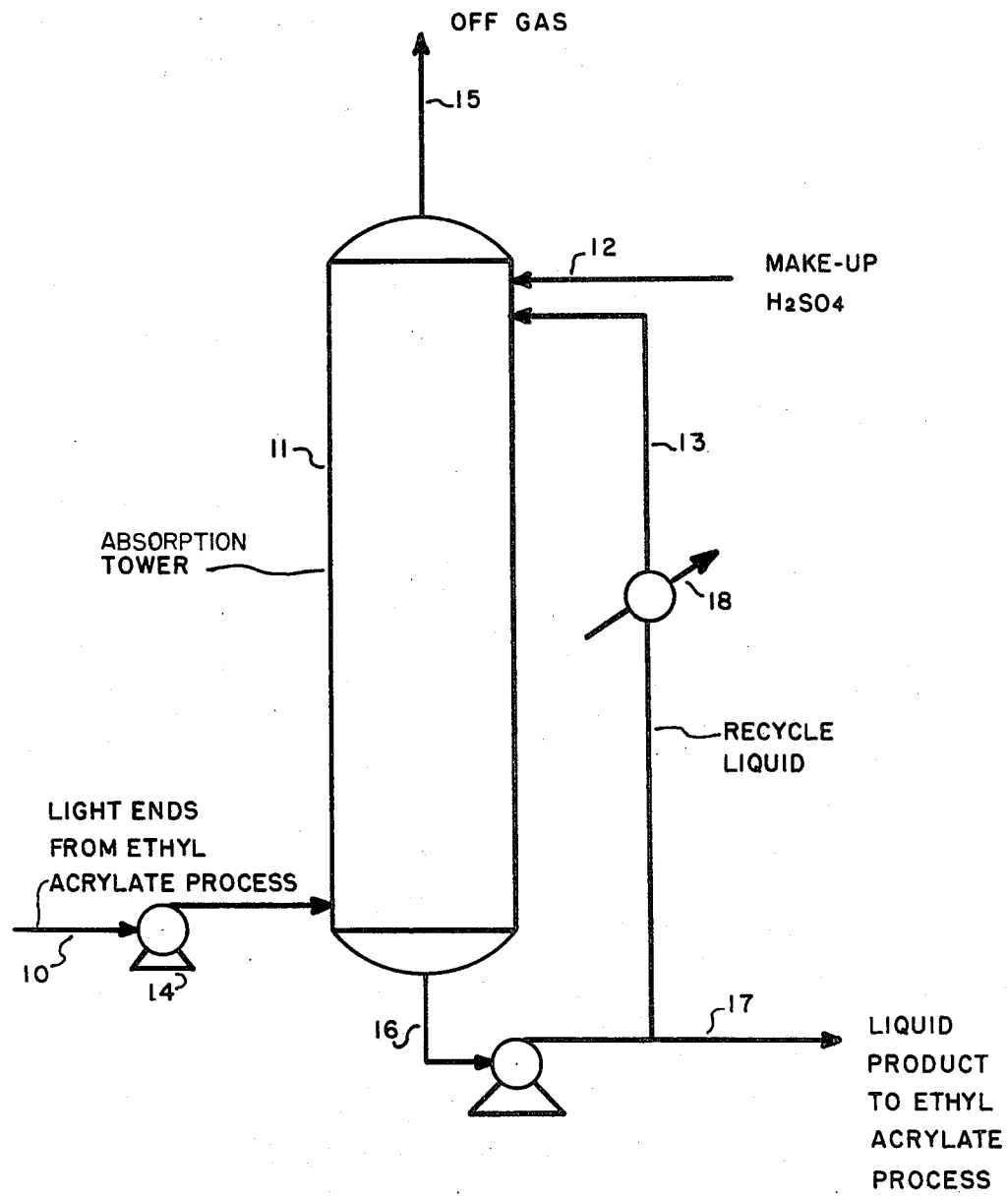

ETHYLENE RECOVERY FROM ETHYL ACRYLATE PROCESS

BACKGROUND OF THE INVENTION

It is known in the prior art to produce ethyl acrylate from ethylene with acrylic acid in the presence of a sulfuric acid catalyst. By way of example, see U.S. Pat. No. 3,894,076 issued July 8, 1975 to Roger L. Van Duyne et al. wherein such a process is disclosed. In these prior art processes recovery of a liquid ethyl acrylate product is accomplished by passing the reaction mixture to a vacuum distillation system wherein, at reduced pressures less than atmospheric, the reaction mixture is distilled to obtain a liquid ethyl acrylate product. Also resulting from the vacuum distillation is a gaseous light ends stream containing sulfur dioxide and also containing ethylene, ethyl acrylate and other organic light ends. The light ends stream may also contain inerts such as nitrogen from air leaks and carbon dioxide from oxidation. The sulfur dioxide in the stream derives from the sulfuric acid catalyst used in reaction of the ethylene with the acrylic acid. Due to losses of sulfuric acid catalyst through sulfur dioxide formation and the like, it is necessary to make up losses of the sulfuric acid by passing a sulfuric acid make-up stream to the process.

Even though the gaseous light ends stream recovered from the vacuum distillation system contains valuable unreacted ethylene, recycle of this stream to recover and use the ethylene therein is not feasible because of the presence of sulfur dioxide in the light ends stream. It has been suggested in the prior art that the light ends stream be scrubbed to remove sulfur dioxide therefrom, and then recycled to the ethyl acrylate reaction zone. Although removal of the sulfur dioxide is possible, the difficulty and expense of accomplishing the removal makes it commercially unfeasible to do so. No economical process has heretofore been presented to recover the ethylene values contained in the light ends stream, and consequently this light ends stream has generally been disposed of and a resulting loss of the ethylene values therein.

It is thus an object of the present invention to provide and disclose a method for treating said gaseous light ends stream from said ethyl acrylate process so as to recover ethylene values contained therein. It is an additional object of the present invention to provide and disclose a method for treating said light ends stream from the ethyl acrylate process so as to recover ethylene values contained therein and recycle same to said ethyl acrylate process without recycling the sulfur dioxide contained in the light ends stream. These and additional objects will become apparent from the following description of the present invention.

SUMMARY OF THE INVENTION

The foregoing and other objects are accomplished by the present invention which, in one of its aspects is an improvement in a continuous process for the production of ethyl acrylate from ethylene and acrylic acid utilizing a sulfuric acid catalyst wherein the reaction products are distilled in a vacuum distillation system at a reduced pressure less than atmospheric to obtain a liquid ethyl acrylate product and also resulting in a first gaseous light ends stream from said vacuum distillation system containing sulfur dioxide and also containing ethylene and other organic light ends, and wherein losses of sulfuric acid catalyst are replenished by continuously passing to the reaction zone of said process of a liquid concentrated sulfuric acid make-up stream consisting of concentrated sulfuric acid having a water content of less than 5% by weight, which improvement comprises: continuously and intimately contacting in a gas-liquid contact zone said first gaseous light ends stream with a reactant liquid consisting essentially of said liquid concentrated sulfuric acid make-up stream and the hereafter defined liquid recycle stream, said contacting being under such conditions as to cause ethylene in said first gaseous light ends stream to react with sulfuric acid in said reactant liquid so as to form ethyl hydrogen sulfate and diethyl sulfate, the said first gaseous light ends stream being at a temperature within the range of about 25° C. to 150° C. when passed to said contact zone, the initial temperature of said reactant liquid being within the range of about 40° C. to 150° C., and the pressure in said contact zone being maintained at a superatmospheric pressure within the range of about 1.05 atmospheres absolute to 20 atmospheres absolute, said pressure being sufficient to maintain said reactant liquid in the liquid phase but insufficient to cause the gases in said first gaseous light ends stream to dissolve in said reactant liquid; continuously withdrawing as overheads from said contact zone a second gaseous light ends stream containing sulfur dioxide, ethylene and other organic light ends, the amount of ethylene in said second gaseous light ends stream being less than the amount in said first gaseous light ends stream, the amount of sulfur dioxide in said second gaseous light ends stream being substantially the same as the amount of sulfur dioxide contained in said first gaseous light ends stream, the temperature of said second gaseous light ends stream being within the range of about 50° C. to 150° C.; continuously withdrawing as bottoms from said contact zone a liquid bottoms product consisting essentially of sulfuric acid having ethyl hydrogen sulfate and diethyl sulfate dissolved therein, said liquid bottoms product being substantially free of sulfur dioxide; and continuously recycling a major portion of said liquid bottoms product to said contact zone as a said liquid recycle stream, and continuously passing a minor portion of said liquid bottoms product to said ethyl acrylate process as a source of make-up sulfuric acid.

DESCRIPTION OF THE DRAWING

The sole FIGURE is a schematic diagram of an embodiment of the invention wherein, in a tower, the gaseous light ends stream is contacted with the liquid sulfuric acid make-up stream.

DETAILED DESCRIPTION OF THE INVENTION

The present invention resides in the discovery that the make-up sulfuric acid stream passed to the reaction zone of the ethyl acrylate process can be used to recover the ethylene values in the gaseous light ends stream. This gaseous light ends stream is normally disposed of with the consequent loss of the ethylene values therein. Typically the light ends stream contains sulfur dioxide and also contains ethylene and other organic light ends, such as ethyl acrylate, ethyl acetate, diethyl ether and ethanol. In most instances some nitrogen and oxygen will also be present due to air leaks in the ethyl acrylate vacuum distillation system, and carbon dioxide may also be present due to oxidation inefficiency. A typical light ends stream will contain at least 10% by weight of sulfur dioxide, usually from about 10 to 30% by weight of sulfur dioxide; and, will also usually contain at least 20% by weight of ethylene, typically from about 20 to 50% by weight of ethylene; and with the remainder of the light ends stream comprising other organic light ends, nitrogen, oxygen, carbon dioxide and the like. It would be desirable to recycle the light ends stream directly to the ethyl acrylate process in order to recover ethylene values therein; however, such cannot be done mainly because of the presence of sulfur dioxide which is an undesired contaminant in the ethyl acrylate process. The presence of the gases such as nitrogen, carbon dioxide and the like also are preferably not recycled to the ethyl acrylate process.

The prior art has suggested removal of the sulfur dioxide contaminant from the light ends stream and the subsequent recycling of the thus decontaminated light ends stream to the ethyl acrylate process. This suggestion has not proved practical from an economic standpoint. Unlike the prior art suggestion of removing the sulfur dioxide from the light ends stream in order that the light ends stream may be recycled, the present invention leaves the sulfur dioxide in the light ends stream and removes only the ethylene values therefrom such that these ethylene values may be recycled to the ethyl acrylate process.

In the present invention the ethylene values are recovered in the form of ethyl hydrogen sulfate and diethyl sulfate which form upon reaction of the sulfuric acid with the ethylene according to the following reactions:

$$H_2SO_4 + C_2H_4 \rightarrow C_2H_5SO_4 \qquad I$$

$$C_2H_5SO_4 + C_2H_4 \rightarrow (C_2H_5)_2SO_4 \qquad II$$

According to Reactions I and II above, two moles of ethylene will be consumed for each one mole of sulfuric acid present; however, Reaction II is an equilibrium reaction such that the actual amount of ethylene utilized will be less than two moles per mole of sulfuric acid present.

The ethyl hydrogen sulfate and diethyl sulfate, upon formation, remain in solution in the make-up sulfuric acid, along with some ethylene which is in simple solution, and are passed to the reaction zone of the ethyl acrylate process along with the make-up sulfuric acid. Once in the reaction zone of the ethyl acrylate process, the ethyl hydrogen sulfate and the diethyl sulfate react directly with acrylic acid to form ethyl acrylate and sulfuric acid.

That sulfuric acid will react with ethylene to form ethyl hydrogen sulfate and diethyl sulfate is known, and it is also known that these two compounds will further react with acrylic acid to form ethyl acrylate. This in fact is the same chemistry involved in the ethyl acrylate process itself as disclosed by the prior art, such as the above referred to U.S. Pat. No. 3,894,076. It has not however been known in the prior art, nor suggested by the prior art, to apply such chemistry to the recovery of ethylene from the light ends stream according to the process of the present invention. Further, from the prior art it would have been unexpected that the reaction to form the sulfates would occur at the temperatures and pressure called for in the present invention (which are relatively low compared to those in the reaction zone of the ethyl acrylate process), and in view of the large amount of sulfur dioxide present in the light ends stream. Sulfur dioxide is generally considered to be a contaminant in the reaction zone of the ethyl acrylate process and it was unexpected that the large amounts of sulfur dioxide in the light ends stream did not prevent or severely inhibit the sulfate formation necessary to the present invention.

Reference is now made to the FIGURE for an explanation of a process conducted in accordance with the present invention. A gaseous light ends stream 10 derived from the vacuum distillation system of the above described ethyl acrylate process is passed to the base of tower 11 while a liquid make-up sulfuric acid stream is fed through line 12 to the upper end of tower 11. Also fed to the upper end of tower 11 is a liquid recycle stream passed through line 13. The make-up sulfuric acid utilized should contain as little water as commercially feasible and in any event should be a concentrated sulfuric acid containing less than 5% by weight of water.

Tower 11 utilized to obtain the intimate contact of the ascending gases with the descending liquid may be any of those of conventional design normally utilized for obtaining intimate gas-liquid contact, such as those used for gas absorption. The tower should however be constructed of a material resistant to the acid medium such as Hastelloy C. The tower may be of packed type or the tray or plate type, the tray or plate type being preferred. The packing or trays should be arranged, and be of an amount or number, so as to assure intimate gas-liquid contact so as to accomplish the required mass transfer of the ethylene into the descending liquid. Where trays or plates are utilized, there should generally be at least about 10 of these trays or plates, with from about 10 to 40 trays or plates generally being sufficient; and, when using packing, the amount of the packing should be that which is roughly equivalent to such number of trays or plates. The liquid to gas ratio should generally be such that the weight of the descending liquid in the tower, that is the combined weight of lines 12 and 13, to the weight of the light ends stream fed through line 10 is at least 5:1, generally within the range of 10:1 to 350:1, and more preferably within the range of 100:1 to 200:1.

The contacting of the liquid with the gas, and thus the conditions within tower 11, should be at temperatures within the range of about 25° C. to 150° C., preferably within the range of about 65° C. to 100° C., and at superatmospheric pressures ranging from slightly above atmospheric, that is about 1.05 atmospheres absolute, to 20 atmospheres absolute, preferably about 1.2 to 10 atmospheres absolute. Since the light ends stream will be taken from a vacuum distillation system operating at subatmospheric pressure, it will be necessary to pass the light ends stream through a compressor 14 for increasing the pressure from subatmospheric to superatmospheric, and this increase in pressure will also cause an increase in the temperature of the gaseous light ends stream.

The foregoing range is of temperatures and pressures are general in nature, and it will be recognized that the temperatures and pressures will not be equal throughout tower 11. The pressure at the base of tower 11 will be greater than at the upper end of the tower by an amount sufficient to overcome the hydraulic pressure of the descending liquid pressure drop due to vapor velocity. Just as the pressure varies at the base and the upper end of the tower, the temperature will also vary, with the gas being cooled as it rises through the tower, and with the descending liquid being heated as it descends in countercurrent contact with the rising gas. Generally the temperature of the gases entering the base of tower 11 through line 10 should be within the range of about 25° C. to 150° C., preferably 65° C. to 100° C. The initial temperature of the descending liquid, that is the liquid resulting from a combination of lines 12 and 13, should be within the range of 40° C. to 150° C. The reaction is slightly exothermic, and the liquid may increase very slightly in temperature after contact with the gas, but the temperature of the liquid withdrawn from the base of tower 11 through line 16 should generally be about the same as that fed to the upper end of the tower. The temperature of the gas removed overhead of tower 11 through overhead line 15 will also be about the same temperature as the liquid fed to the upper end of the tower.

The temperature and pressure control is very important to the operation of the present invention, and the desired results will not be obtained unless temperature and pressure are properly controlled. The pressure is important in that too much pressure will cause various components of the light ends stream to dissolve in the sulfuric acid medium, with these components thus ultimately being returned to the reaction zone of the ethyl acrylate process where they will lower the efficiency of the process. On the other hand, if the pressure is too low then the amount of ethylene absorbed into the sulfuric acid medium will be insufficient, and the recovery of ethylene values will be minimal. Operating at too high a temperature will result in carbon dioxide formation from the ethylene since the sulfuric acid is a strong oxidizer. High temperatures will also cause polymerization of components present in the light ends stream. If temperatures are too low, then the desired reaction of the ethylene with the sulfuric acid to form the sulfates will be inhibited.

Of the liquid removed as a bottoms stream through line 16, a major portion thereof will be recycled through line 13 to the upper end of tower 11, while a minor portion will be removed through line 17 and passed to the reaction zone of the ethyl acrylate process as a source of make-up sulfuric acid. The volume of liquid removed through the line 17 will be roughly the same as the fresh make-up sulfuric acid fed through line 12, although the weight per unit time of these sulfate enriched liquids removed through line 17 will be slightly higher than the weight per unit volume of the fresh make-up sulfuric acid through line 12. The weight per unit time of gases removed overhead of tower 11 through line 15 will be less than the weight per unit time of the light ends stream fed through line 10 due to the removal of ethylene. Generally, about 50 to 98% of the liquid bottoms removed through line 16 will be recycled through line 13, with the remainder being withdrawn through line 17. The amount of line 16 will be about the amount of liquid passed to the upper end of the tower, plus the ethylene absorbed from line 10. The temperature of the liquid bottoms recycled through line 13 will be controlled by heat exchanger 18 prior to being recycled to the upper end of tower 11.

The liquid recycle through line 13 is very important, and is critical to operation of the process, for several reasons. First, the make-up sulfuric acid through line 12 is too small a stream to provide good gas-liquid contact. Secondly the recycle stream has a relatively low concentration of sulfuric acid (as compared to the make-up stream) because of the presence of ethyl hydrogen sulfate and diethyl sulfate, and this lower concentration of sulfuric acid will diminish the danger of ethylene polymerization or decomposition. Thirdly, the presence of ethyl hydrogen sulfate in the recycle increases the ethylene absorption in the liquid.

By operating according to the present invention, usually about 65% to 85% of the ethylene contained in the light ends stream can be recovered, more usually about 70% to 75%. The following example is given to illustrate the present invention, but is not to be taken as limiting the scope thereof.

EXAMPLE

To an apparatus of the type illustrated in the FIGURE, there was passed to tower 11 through line 10 about 360 grams per hour of a synthetic feed similar to the gaseous light ends from the above described ethyl acrylate process. The gases flowing through line 10 were at a temperature of about 90° C. and a pressure of about 2 atmospheres absolute after passing through compressor 14. The gaseous light ends stream contained, by weight, about 30% ethylene, 30% sulfur dioxide, and 40% nitrogen.

Tower 11 was approximately 1.5 meters in height and 5 centimeters in diameter and contained 15 trays of the sieve type. The pressure at the base of tower 11 was about 2.03 atmospheres absolute and pressure at the upper end of tower 11 was about 2.00 atmospheres absolute. The gaseous light ends stream passed through line 10 to the bottom of tower 11 entered at a point below the lower tray. Passed to the upper end of tower 11, at a point above the uppermost tray, through line 12 was about 480 grams per hour of fresh make-up sulfuric acid having a concentration of about 97%, the remaining 3% comprising water. Also fed onto the upper tray of tower 11 through line 13 was about 15 kilograms per hour of recycle liquid. The temperature of the fresh make-up sulfuric acid fed through line 12 was 30° C., while the temperature of the liquid recycle fed to the tower through line 13 was 70° C. after having passed through heat exchanger 18.

About 15.6 kilograms per hour of liquid bottoms was removed through line 16, such having a temperature of about 75° C. upon removal from the lower end of tower 11, with about 15 kilograms per hour of the liquid bottoms being recycled through line 13 as mentioned above, and the remaining 0.6 kilograms per hour being withdrawn through line 17 as a source of make-up sulfuric acid for the ethyl acrylate process. The product withdrawn through line 17 consisted essentially of sulfuric acid having about 50% by weight of ethyl hydrogen sulfate and 5% by weight of diethyl sulfate dissolved therein, and this product was substantially free of sulfur dioxide.

The overhead gases removed through line 15 were at a temperature of 70° C. and had a composition, by weight, of about 12% ethylene, 0.1% ethanol, 38% sulfur dioxide, and 50% nitrogen. The amount of sulfur dioxide in the gases removed through line 15 was substantially the same as that passed to the lower end of tower 11 through line 10, however, only about 30% of the ethylene in line 10 appeared in the overhead gases removed through line 15, the remaining 70% having been recovered in the form of ethyl hydrogen sulfate and diethyl sulfate through line 17.

The embodiments of the invention in which an exclusive claim or privilege is claimed are:

1. In a continuous process for the production of ethyl acrylate from ethylene and acrylic acid utilizing a sulfuric acid catalyst wherein the reaction products are distilled in a vacuum distillation system at a reduced pressure less than atmospheric to obtain a liquid ethyl acrylate product and also resulting in a first gaseous light ends stream from said vacuum distillation system containing sulfur dioxide and also containing ethylene and other organic light ends, and wherein losses of sulfuric acid catalyst are replenished by continuously passing to the reaction zone of said process a sulfuric acid make-up stream consisting of concentrated sulfuric acid having less than five percent by weight of water therein, the improvement which comprises: continuously and intimately contacting in a gas-liquid contact zone said first gaseous light ends stream with a reactant liquid consisting essentially of said liquid sulfuric acid make-up stream and the hereafter defined liquid recycle stream, said contacting being under such conditions as to cause ethylene in said first gaseous light ends stream to react with sulfuric acid in said reactant liquid so as to form ethyl hydrogen sulfate and diethyl sulfate, the said first gaseous light ends stream being at a temperature within the range of about 25° C. to 150° C. when passed to said contact zone, the initial temperature of said reactant liquid being within the range of about 40° C. to 150° C., and the pressure in said contact zone being maintained at a superatmospheric pressure within the range of about 1.05 atmospheres absolute to 20 atmospheres absolute, said pressure being sufficient to maintain said reactant liquid in the liquid phase but insufficient to cause the gases in said first gaseous light ends stream to dissolve in said reactant liquid; continuously withdrawing as overheads from said contact zone a second gaseous light ends stream containing sulfur dioxide, ethylene and other organic light ends, the amount of ethylene in said second gaseous light ends stream being less than the amount in said first gaseous light ends stream, the amount of sulfur dioxide in said second gaseous light ends stream being substantially the same as the amount of sulfur dioxide contained in said first gaseous light ends stream, the temperature of said second gaseous light ends stream being within the range of about 50° C. to 150° C.; continuously withdrawing as bottoms from said contact zone a liquid bottoms product consisting essentially of sulfuric acid having ethyl hydrogen sulfate and diethyl sulfate dissolved therein, said liquid bottoms product being substantially free of sulfur dioxide; and continuously recycling a major portion of said liquid bottoms product to said contact zone as a said liquid recycle stream, and continuously passing a minor portion of said liquid bottoms product to said ethyl acrylate process as a source of make-up sulfuric acid.

2. The process of claim 1 wherein said major portion of said liquid bottoms product comprises from about 50 to 98% by weight of the total of said liquid bottoms product.

3. The process of claim 1 wherein the said contacting of said reactant liquid with said first gaseous light ends stream is accomplished in a said contact zone consisting of a tower wherein the first gaseous light ends stream ascends in said tower counter-currently to and in intimate contact with descending reactant liquid, the weight ratio of said reactant liquid to said first gaseous light ends stream being at least 10:1.

4. The process of claim 1 wherein said first gaseous light ends stream contains at least 10% by weight of sulfur dioxide and contains at least 20% by weight of ethylene.

* * * * *